(12) United States Patent
Peters et al.

(10) Patent No.: US 8,101,569 B2
(45) Date of Patent: *Jan. 24, 2012

(54) ENERGY STATUS OF AN INDIVIDUAL BY ENHANCED PRODUCTION OF AN ENDOGENOUS FUEL SOURCE

(75) Inventors: Jason Peters, Oakville (CA); Michele Molino, Oakville (CA)

(73) Assignee: Northern Innovations and Formulations, Inc., Oakville, ON (CA)

( * ) Notice: Subject to any disclaimer, the term of this patent is extended or adjusted under 35 U.S.C. 154(b) by 0 days.

This patent is subject to a terminal disclaimer.

(21) Appl. No.: 12/829,438

(22) Filed: Jul. 2, 2010

(65) Prior Publication Data
US 2011/0059906 A1    Mar. 10, 2011

Related U.S. Application Data

(63) Continuation of application No. 11/867,433, filed on Oct. 4, 2007, now Pat. No. 7,820,618.

(51) Int. Cl.
| | | |
|---|---|---|
| A61K 38/28 | (2006.01) |
| A61K 31/522 | (2006.01) |
| A61K 31/20 | (2006.01) |
| A61K 31/195 | (2006.01) |
| A61K 31/19 | (2006.01) |

(52) U.S. Cl. .............. 514/5.9; 514/263.34; 514/560; 514/561; 514/565; 514/570

(58) Field of Classification Search .............. 514/5.9, 514/263.34, 560, 561, 565, 570
See application file for complete search history.

(56) References Cited

U.S. PATENT DOCUMENTS
7,820,618 B2 * 10/2010 Peters et al. .............. 514/6.5
* cited by examiner

*Primary Examiner* — Raymond Henley, III

(57) ABSTRACT

The present invention relates to a method of improving the energy status of an individual by enhancing the usage of lactate. Improved lactate usage is accomplished through a composition comprising lactate precursors, adrenergic receptor agonists and insulinotropic agents.

30 Claims, No Drawings

ENERGY STATUS OF AN INDIVIDUAL BY ENHANCED PRODUCTION OF AN ENDOGENOUS FUEL SOURCE

The application is related to the applicant's U.S. patent application Ser. No. 11/867,433 entitled "Improving the Energy Status of an Individual by Enhanced Usage of an Endogenous Fuel Source" filed Oct. 4, 2007, now issued as U.S. Pat. No. 7,820,618, which is herein fully incorporated by reference.

FIELD OF THE INVENTION

The present invention relates to methods and compositions for improving the energy status of an individual by enhancing the usage of an endogenously produced energy source.

BACKGROUND OF THE INVENTION

There are three main metabolic pathways utilized by humans to produce energy in the form of adenosine triphosphate (ATP): oxidative respiration, anaerobic glycolysis and the phosphagen system (Lanza I R, Befroy D E, Kent-Braun J A. Age-related changes in ATP-producing pathways in human skeletal muscle in vivo. J Appl Physiol. 2005 November; 99(5):1736-44).

Under conditions where oxygen is available, oxidative respiration in the mitochondria generates ATP. Aerobic metabolism involves a complicated series of reactions to produce energy. In terms of efficiency, aerobic metabolism provides more energy than anaerobic metabolism. Aerobic respiration is used to provide energy during endurance-type activities which are typified by low- to moderate-intensity activities maintained for long durations (Korzeniewski B. Regulation of oxidative phosphorylation in different muscles and various experimental conditions. Biochem J. 2003 Nov. 1; 375(Pt 3):799-804).

Anaerobic glycolysis is utilized for energy when aerobic metabolism becomes limiting for ATP production as occurs during strenuous physical activity. Anaerobic metabolism is considerably less efficient than aerobic metabolism, in terms of energy produced. Anaerobic glycolysis is typically needed to produce energy when the oxygen supply to muscle is limited, such as during short duration high-intensity activity (Casey A, Greenhaff P L. Does dietary creatine supplementation play a role in skeletal muscle metabolism and performance? Am J Clin Nutr. 2000 August; 72(2 Suppl):607S-17S).

Phosphocreatine is the phosphagen utilized by humans to store energy in a form that can quickly be used to regenerate ATP. The enzyme creatine kinase catalyzes a reversible reaction in which phosphocreatine is used as a source of phosphate to regenerate ATP from ADP (adenosine phosphate). Phosphocreatine provides a rapid source of ATP but is very limited, only supplying enough energy for a few seconds of high-intensity activity.

Both aerobic and anaerobic metabolisms share the initial steps of substrate processing, whereby blood glucose or muscle glycogen is converted to pyruvate. In the presence of adequate oxygen pyruvate is then used in the citric acid cycle, also known as the Krebs cycle. Glycolysis can proceed so quickly that pyruvate accumulates in the muscle. When this accumulation of pyruvate occurs, the enzyme lactate dehydrogenase converts pyruvate to lactate (Gladden L B. Lactic acid: New roles in a new millennium. Proc Natl Acad Sci USA. 2001 Jan. 16; 98(2):395-7). Lactate, in turn, is used to regenerate nicotinamide adenine dinucleotide (NAD+), an important cofactor needed for glycolysis (Robergs R A, Ghiasvand F, Parker D. Biochemistry of exercise-induced metabolic acidosis. Am J Physiol Regul Integr Comp Physiol. 2004 September; 287(3):R502-16).

Traditionally, Lactic acid has been thought to be a toxic waste product responsible for muscle fatigue, reduced performance and muscle pain following intense exercise. This has largely been due to the coincidental lowered pH associated with intense exercise and increased muscle lactate. As such, this has been termed "lactic acidosis" and has been theorized to be caused by the production of lactic acid, which acidifies or lowers the pH by losing a proton ($H^+$) in bodily tissues and fluids.

A more recent re-interpretation of previous findings in light of new data suggests that lactic acid may in fact not be the cause of the aforementioned exercise-induced metabolic acidosis (Robergs R A, Ghiasvand F, Parker D. Biochemistry of exercise-induced metabolic acidosis. Am J Physiol Regul Integr Comp Physiol. 2004 September; 287(3):R502-16). The accumulation of inorganic phosphate and protons, mostly from the hydrolysis of ATP at a rate which exceeds that of ATP regeneration, is supported by evidence to be more likely than lactic acid as the cause of exercise-induced metabolic acidosis.

G. Brooks in an abstract from the 2006 Journal of the International Society of Sports Nutrition Conference Proceeding discloses that the shuttling of lactate through the interstitium and vasculature provides a significant carbon source for oxidation and gluconeogenesis during rest and exercise. Furthermore, adding to the original idea that lactate released from fast glycolytic fibers fuels slow-oxidative fibers, it known now that lactate is shuttled between different cells, organs and tissues to provide an energetic function. Lactate, due to recent evidence is being viewed as an essential component of intermediary metabolism and no longer a metabolic waster product (Brooks G. The Lactate Shuttle. International Society of Sports Nutrition Conference Proceedings. Journal of the International Society of Sports Nutrition. 2006. 3(1)S30-S43).

Therefore, in fact, the cellular presence and production of lactate, or lactic acid, has been suggested to be beneficial for prolonging exercise (Messonnier L, Denis C, Feasson L, Lacour J R. An elevated sarcolemmal lactate (and proton) transport capacity is an advantage during muscle activity in healthy humans. J Appl Physiol. 2006 Jul. 27; [Epub ahead of print]). It should be noted that "lactic acid" does not exist as an acid under normal physiological conditions but rather as a lactate anion. Additionally, not only does the production of lactate assist in the regeneration of NAD+ but it also consumes a proton which buffers against metabolic acidosis, As such, lactate likely does not cause or contribute to metabolic acidosis. Furthermore, lactate has been shown to be a key fuel source and the concept of the "lactate shuttle" has been largely supported by experimental evidence (Brooks G A. Lactate shuttles in nature. Biochem Soc Trans. 2002 April; 30(2):258-64). The term "lactate shuttle" as used herein refers to the transport or "shuttling" of lactate, both intracellularly and intercellularly. One of the main observations has been that endurance/aerobic training reduces blood lactate levels despite the continued production of lactate from muscle cells, thus giving rise to the concept that, against traditional thinking, lactate and the lactate shuttle must contribute as fuel source to working muscles.

The lactate shuttle is facilitated by membrane-bound monocarboxylate transporters (MCTs). In skeletal muscle, two distinct isoforms have been characterized—MCT-1 and MCT-4, each with different properties. Training has been shown to have effects on the expression of MCTs resulting in more efficient use of lactate, particularly with respect to the clearance of lactate from the blood by increasing its uptake within cells (Dubouchaud H, Butterfield G E, Wolfel E E, Bergman B C, Brooks G A. Endurance training, expression, and physiology of LDH, MCT1, and MCT4 in human skeletal muscle. Am J Physiol Endocrinol Metab. 2000 April; 278(4): E571-9).

Most lactate is removed through oxidation while the remainder is converted to glucose and glycogen. The hypothesis of the lactate shuttle holds that excess lactate transported both intracellularly (via an intracellular lactate shuttle) and intercellularly (via a cell-to-cell lactate shuttle) for use as immediate fuel or for storage (Gladden L B. Lactate metabolism: a new paradigm for the third millennium. J Physiol. 2004 Jul. 1; 558(Pt 1):5-30). Muscles at rest produce and release low levels of lactate with little uptake. During periods of short duration but high-intensity muscle activity, muscles produce and release higher levels of lactate into the blood. During recovery, or during low- to moderate-intensity activity, muscles show a net increase in the uptake of lactate from the blood. Within cells lactate produced from glycolysis is transported from the cytosol into the mitochondria where it is subsequently converted to pyruvate. As pyruvate, it can be utilized in the citric acid cycle.

As there is a need, it would therefore be advantageous to increase the availability and usage of lactate, either through endogenous mechanisms, or through exogenous sources. By increasing the production of lactate within a cell, the intracellular lactate shuttle may be utilized to supply the cell with increased energy. Moreover, by concomitantly increasing the production and/or secretion of lactate from a given cell and increasing the uptake of lactate by another cell, the cell-to-cell lactate shuttle may be utilized to supply additional, distal cells with increased energy. It would therefore be advantageous to improve the energy supply to muscle and other bodily systems, organs, tissues or cells through enhancing the production and utilization of endogenous fuel sources i.e. lactate, in a mammal.

SUMMARY OF THE INVENTION

The foregoing needs and other needs and objectives that will become apparent for the following description are achieved in the present invention which comprises methods and compositions for improving the energy status of a mammal, by enhancing the usage of lactate in said mammal wherein the usage of lactate is enhanced via the administration of an adrenergic receptor agonist and by an insulinotropic agent. Furthermore, usage of lactate is enhanced by the administration lactate, lactate analogues, or precursors of lactate.

DETAILED DESCRIPTION OF THE INVENTION

In the following description, for the purposes of explanations, numerous specific details are set forth in order to provide a thorough understanding of the present invention. It will be apparent, however, to one skilled in the art that the present invention may be practiced without these specific details.

As used herein, the term "nutritional composition" includes dietary supplements, diet supplements, nutritional supplements, supplemental compositions and supplemental dietary compositions or those similarly envisioned and termed compositions not belonging to the conventional definition of pharmaceutical interventions as is known in the art. Furthermore, "nutritional compositions" as disclosed herein belong to the category of compositions having at least one physiological function when administered to a mammal by conventional routes of administration. The dosage form of the nutritional composition may be provided in accordance with customary processing techniques for herbal and nutritional compositions in any of the forms mentioned above. Additionally, the nutritional composition set forth in the example embodiment herein disclosed may contain any appropriate number and type of excipients, as is well known in the art.

As it is used herein, the terms "lactate usage" or "usage of lactate" refers to the involvement of lactate as an energy source. It is understood that the usage of lactate may be enhanced or improved by a number of non-mutually exclusive mechanisms including, but not limited to; increased availability of lactate or lactate precursors, increased production or synthesis of lactate or lactate precursors, increased secretion of lactate or lactate precursors from cells, increased transport of lactate or lactate precursors within or between cells and enhanced uptake of lactate or lactate precursors by cells. Other mechanisms of improving lactate usage will be apparent to one of skill in the art.

As used herein, the term "derivatives of" refers to any compound resulting from modification to the referred parent compound. In is herein understood that the modifications for producing derivatives are numerous and include but are not limited to; esterification, acetylation, silylatiion and alkylation. Those of skill in the art will readily recognize additional reactions suitable for producing derivatives. Such reactions are known to improve parameters such as stability or absorption. The term "derivatives of" also refers to compounds commonly referred to as pro-drugs, which are inactive precursors of active compounds that become active within the body after reaction with endogenous metabolic processes. Furthermore, the term "derivatives of" also refers to precursors of parent compounds that will be reacted within the body by endogenous metabolic processes to form the parent compound.

As used herein, the term "insulinotropic" refers to any process, activity or effect resulting in an increase in the activity of insulin. This is usually through increasing the production and secretion of insulin but as used herein, the term "insulinotropic" also includes other mechanisms of increasing the activity of insulin which may include but are not limited to: increasing the binding of insulin, increasing the stability of insulin and increasing the plasma half-life of insulin.

The present invention provides a method for improving the energy status of a mammal, by increasing the usage of a natural endogenous fuel source in said mammal. Specifically, the present invention provides a mechanism of improving the energy status of a mammal, by increasing the usage of lactate in said mammal. By way of enhancing the use of lactate there will result an overall improvement in the energy status of said mammal, both at times of rest and during physical activity, particularly during strenuous physical activity. The improved energy status will be of benefit to both cells directly involved in said physical activity e.g. skeletal muscle cells and cardiac muscle cells, and cells which may not be directly involved in physical activity such as, for example, liver cells, unrecruited skeletal muscle cells including, but not limited to myocytes and satellite cells, and brain cells including, but not limited to neurons, glial derived cells such as microglia and astroglia, and oligodendrial cells, via transmission of lactate through the circulatory system.

Lactate/Lactic Acid

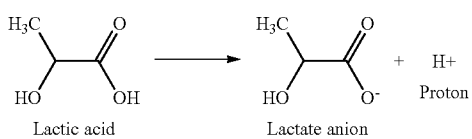

Lactic acid          Lactate anion

Lactic acid (CAS 50-21-5) is a constant and normal product of metabolism and exercise. Under typical conditions of physiological pH, nearly all lactic acid dissociates into lactate (lactate⁻ anion) and protons (H⁺).

For the purposes of the present invention, lactate-precursors can be employed as a method to elevate bodily lactate levels. It is understood by the inventors that increasing the bioavailability of endogenous precursors of lactate will increase the conversion of lactate precursors to lactate, thereby increasing the net bioavailable levels of lactate.

Certain embodiments of the present invention comprise pyruvate or derivatives of pyruvate as a precursor of lactate. Pyruvate and lactate are capable of interconversion (Philp A, Macdonald A L, Watt P W. Lactate—a signal coordinating cell and systemic function. J Exp Biol. 2005 December; 208 (Pt 24):4561-75). The amount of pyruvate or derivatives of pyruvate in a serving of the composition of the present invention is from about 1 mg to 1000 mg.

Other embodiments of the present invention comprise glutamine, which can be metabolized to increase lactate, or derivatives of glutamine. The amount of glutamine or derivatives of glutamine in a serving of the present invention are from about 0.05 g to about 5.00 g.

It is understood that those of skill in the art will recognize additional suitable lactate precursors that are included within the scope of the present invention.

Adrenergic Receptors

Adrenergic receptors are a class of receptors which respond to catecholamines. Catecholamines are a class of chemical compounds derived from the amino acid tyrosine. Furthermore, the most abundant catecholamines are the neurotransmitters epinephrine, norepinephrine and dopamine.

Epinephrine, also known as adrenaline, is both a hormone and neurotransmitter. The principle role of epinephrine lies within the realm of stress responses. Epinephrine binds to and stimulates alpha-adrenergic receptors in liver cells and beta-adrenergic receptors in liver and muscle cells. Propanolol, a pharmacological agent is a beta-adrenergic receptor blocker commonly used to counter the effects of epinephrine and to treat hypertension.

Research has demonstrated that epinephrine increases production and release of lactate from human cells (Lockette W, Kirkland K, Farrow S. Alpha 2-adrenergic agonists increase cellular lactate efflux. Hypertension. 1996 May; 27(5):1104-7). Moreover, in trained males undergoing exercise, epinephrine has been shown to increase both muscle and plasma lactate levels which coincided with enhanced glycogen utilization, glycolysis, and carbohydrate oxidation in muscle (Febbraio M A, Lambert D L, Starkie R L, Proietto J, Hargreaves M. Effect of epinephrine on muscle glycogenolysis during exercise in trained men. J Appl Physiol. 1998 February; 84(2):465-70) indicating a putative role as a muscular fuel source. Interestingly, patients diagnosed with obstructive sleep apnea syndrome display abnormally high levels of epinephrine relative to normal controls. When these patients exercise, lactate production is increased relative to controls, thus providing a further correlation between epinephrine to lactate production (Bonanni E, Pasquali L, Manca M L, Maestri M, Prontera C, Fabbrini M, Berrettini S, Zucchelli G, Siciliano G, Murri L. Lactate production and catecholamine profile during aerobic exercise in normotensive OSAS patients. Sleep Med. 2004 March; 5(2):137-45). It is understood that a blockade of beta-andrenergic receptors in humans results in a combination of decreased lactate production and decreased lactate uptake after intense exercise (Kaiser P, Tesch P A. Effects of acute beta-adrenergic blockade on blood and muscle lactate concentration during submaximal exercise. Int J Sports Med. 1983 November; 4(4):275-7).

Beta-adrenergic receptor agonists also show potential use at promoting increases in muscle growth or hypertrophy, particularly for the treatment of muscle-wasting disorders, sacropenia, or muscle injury (Beitzel F, Gregorevic P, Ryall J G, Plant D R, Sillence M N, Lynch G S. Beta2-adrenoceptor agonist fenoterol enhances functional repair of regenerating rat skeletal muscle after injury. J Appl Physiol. 2004 April; 96(4):1385-92). Stimulation of beta-adrenergic receptors causes increases in intracellular levels of the messenger molecule cyclic adenosine monophosphate (cAMP), important for intracellular signal transduction.

Since antagonism or blockage of beta-adrenergic receptors inhibits the uptake of lactate by cells and possibly its production, it is understood by the inventor that stimulation of said receptors would stimulate lactate uptake. Therefore, agents which stimulate alpha- and beta-adrenergic receptors or beta-adrenergic receptors alone i.e. adrenergic agonists, may stimulate the production, release and uptake of lactate by cells where the lactate could be used for immediate energy or converted to glycogen for storage. Therefore, it would be advantageous to use agents which increase the activity of adrenergic receptors to enhance the usage of lactate as a fuel source.

Caffeine has been found to increase the production of lactate in healthy humans (Astrup A, Toubro S, Cannon S, Hein P, Breum L, Madsen J. Caffeine: a double-blind, placebo-controlled study of its thermogenic, metabolic, and cardiovascular effects in healthy volunteers. Am J Clin Nutr. 1990 May; 51(5):759-67) Therefore, caffeine, via increasing epinephrine, an alpha- and beta-adrenergic agonist, can increase the production and release of lactate.

It is herein understood that increasing adrenergic receptor activity via adrenergic receptor agonists may be accomplished through a number of non-mutually exclusive mechanisms including but not limited to; increasing the levels of adrenergic receptor protein-coding mRNA, increasing the levels of adrenergic receptors via the increased expression of new receptor proteins, increasing the functional biological activity of pre-existing receptor proteins, and increasing the availability or activity of adrenergic receptor substrate. Other mechanisms of increasing the activity of adrenergic receptors will be apparent to those of skill in the art.

Various embodiments of the present invention comprise caffeine or derivatives of caffeine as an agent with adrenergic agonist activity. A serving of the present invention comprises from about 5 mg to about 500 mg of caffeine or derivatives of caffeine.

Other embodiments of the present invention comprise epinephrine or derivatives of epinephrine as an agent with adrenergic agonist activity. A serving of the present invention comprises from about 0.01 mg to about 1 mg of epinephrine or derivatives of epinephrine.

Other embodiments of the present invention comprise norepinephrine or derivatives of norepinephrine as an agent with adrenergic agonist activity. A serving of the present invention comprises from about 0.01 mg to about 1 mg of norepinephrine or derivatives of norepinephrine.

Other embodiments of the present invention comprise dopamine or derivatives of dopamine as an agent with adrenergic agonist activity. A serving of the present invention comprises from about 0.01 mg to about 2 mg of dopamine or derivatives of dopamine.

It is herein understood that alpha- and beta-adrenergic agonists, either alone or in combination will enhance the usage of lactate as an energy source. It is further understood that the specific adrenergic agonists herein described represent examples and are in no way construed to be in any way limiting. Other suitable adrenergic agonists will be known to those of skill in the art and are within the scope of the present invention.

Insulin and Insulinotropic Activity

Insulin is a hormone secreted by the pancreas in humans in response to glucose in the plasma and is involved in glucose uptake, thereby lowering blood glucose levels. Postprandial blood glucose levels rise and stimulate the secretion of insulin.

It has been shown that high levels of insulin induce increased lactate production in cultured human cells (Lockette W, Kirkland K, Farrow S. Alpha 2-adrenergic agonists increase cellular lactate efflux. Hypertension. 1996 May; 27(5):1104-7). In healthy humans, increases in insulin levels have been shown to stimulate the release of lactate from skeletal muscle, which is further enhanced in endurance-trained individuals (Juel C, Holten M K, Dela F. Effects of strength training on muscle lactate release and MCT1 and MCT4 content in healthy and type 2 diabetic humans. J Physiol. 2004 Apr. 1; 556(Pt 1):297-304). This release of lactate is proportional to glucose uptake and, in the case of exercise, involves an increase in the content of MCTs. Furthermore, ingestion of carbohydrate, which is well known to induce insulin secretion, and exercise each separately increase blood lactate levels in humans (Stevenson E J, Williams C, Mash L E, Phillips B, Nute M L. Influence of high-carbohydrate mixed meals with different glycemic indexes on substrate utilization during subsequent exercise in women. Am J Clin Nutr. 2006 August; 84(2):354-60). Therefore, an exercise-induced increase in lactate levels, which will benefit energy status, will be enhanced by agents that increase the activity of insulin.

A number of dietary constituents other than glucose are known to stimulate insulin secretion. Certain amino acids, such as arginine, or amino acid combinations, such as leucine and glutamine, have also been shown to increase the secretion of insulin from cultured normal human pancreatic cells (Henquin J C, Dufrane D, Nenquin M. Nutrient control of insulin secretion in isolated normal human islets. Diabetes. 2006 December; 55(12):3470-7). Leucine by itself is known to be the most insulinotropic agent, with the exception of glucose (MacDonald M J, McKenzie D I, Kaysen J H, Walker T M, Moran S M, Fahien L A, Towle H C. Glucose regulates leucine-induced insulin release and the expression of the branched chain ketoacid dehydrogenase E1 alpha subunit gene in pancreatic islets. J Biol Chem. 1991 Jan. 15; 266(2): 1335-40). Esters of succinic acid, a precursor of glucose and an intermediate of the energy-producing citric acid cycle, have been shown to have strong insulinotropic activity (Zawalich W S, Zawalich K C. Biochemical mechanisms involved in monomethyl succinate-induced insulin secretion. Endocrinology. 1992 August; 131(2):649-54). Furthermore, a specific derivative of pyruvate, methyl pyruvate, has demonstrated insulinotropic activity isolated rat pancreas cells (Zawalich W S, Zawalich K C. Influence of pyruvic acid methyl ester on rat pancreatic islets. Effects on insulin secretion, phosphoinositide hydrolysis, and sensitization of the beta cell. J Biol Chem. 1997 Feb. 7; 272(6):3527-31).

Embodiments of the present invention comprise compounds possessing insulinotropic effects. A number of specific examples of insulinotropic agents have been discussed and it is herein understood that other suitable insulinotropic agents also within the scope of the present invention will be apparent to those of skill in the art. The insulinotropic agents are present in amounts sufficient to cause an effective increase in blood insulin levels.

Therefore, in terms of energy and lactate usage it is advantageous to supply supplemental sources of lactate such as lactate salts or lactate-precursors in combination with agents that increase adrenergic receptor activity or agents with insulinotropic activity that will act to enhance the usage of lactate.

According to various embodiments of the present invention, the nutritional composition may be consumed in any form. For instance, the dosage form of the nutritional composition may be provided as, e.g. a powder beverage mix, a liquid beverage, a ready-to-eat bar or drink product, a capsule, a liquid capsule, a tablet, a caplet, or as a dietary gel. The preferred dosage forms of the present invention are provided as a capsule or as a liquid capsule.

According to various embodiments of the present invention, the nutritional supplement may be administered in a dosage form with controlled release characteristics i.e. time-release. Furthermore, the controlled release may be in the form of either delayed release of active constituents or gradual, prolonged release i.e. sustained-release. The goal of such strategies is to extend the period of bioavailability or to meet a specific window for optimal bioavailability. Advantageously the nutritional supplement may be administered in the form of a multi-compartment capsule which combines both immediate release and time-release characteristics. Differential release characteristics may be achieved through modifications to the active constituents, through specific properties of the compartments, the use of specific excipients with desired properties, or a combination of these. The compartments of such a multi-compartment capsule may be defined by physical divisions within the capsule or smaller spatial units within the capsule or compartments of the capsule such as beads or beadlets. Individual components of the nutritional supplement may be contained in differential compartments of such a capsule such that specific components are released rapidly while others are time-released. Alternatively, a uniform mix of the various components of the present invention may be divided into both immediate release and time-release compartments to provide a multi-phasic release profile.

Further embodiments of the present invention may employ particle-milling technology for enhanced utility and efficacy. U.S. patent application Ser. No. 11/709,526 entitled "Method For Increasing The Rate And Consistency Of Bioavailability Of Supplemental Dietary Ingredients" filed Feb. 21, 2007, which is herein fully incorporated by reference discloses the use of particle-milling for the purposes of increasing the rate of bioavailability following oral administration of components comprising supplemental dietary compositions. The increased bioavailability of a compound or ingredients is achieved via a reduction in particle size using a "fine-milling" technique. For the purposes of the present invention, the terms micronization, milling, particle-milling, and fine-milling are used interchangeably, wherein they refer to a technology, process and end-products involved in or leading to a narrowing of particle size range and a concomitant reduction in the average particle size. For the purposes of the present invention, acceptable milled-particle sizes are in the range of from about 1 nanometer to about 500 microns. Further to improving bioavailability, it is understood by the inventors that increased solubility resulting from fine-milling will lead to improvements in characteristics in which solubility and reduced particle size likely play a role. The components of the present invention may be fine-milled in order to quicken the rate of dissolution.

Additionally, U.S. patent application Ser. No. 11/709,525 entitled "Method for a Supplemental Dietary Composition Having a Multi-Phase Dissolution Profile" filed Feb. 21, 2007, also herein fully incorporated by reference, discloses that components of the present invention may be used as portions of both non-milled and fine-milled, in order to provide a bi-phasic dissolution profile.

Conventional oral dosage formulations are bound by the rate of dissolution of the unprocessed substance, thereby limiting the rate of bioavailability of the substance upon oral administration. This is particularly problematic for poorly-soluble compounds which have an inherently low rate of dissolution in that they may be excreted prior to first-pass.

It is herein understood that, due to the relationship between solubility and dissolution, the amount of a substance in solution at any given time is dependent upon both dissolution and solubility. Furthermore, it is understood by way of extension that increasing the rate of dissolution of a given substance acts to reduce the time to dissolution of a given solute or substance in a given solvent. However, the absolute solubility of said solute does not increase with infinite time. Thus, increasing the rate of dissolution of a substance will increase the amount of said substance in solution at earlier points in time, thus increasing the rate of bioavailability of said substance at earlier times upon oral administration. The increase in the rate of bioavailability will allow better and quicker compound transfer to the systemic parts of the body.

Micronization is a technique which has been used as a method of sizing solid compounds to fine powders. Following a micronization process, compounds and more specifically poorly soluble compounds are transformed into fine powders which can then be transformed into suitable, stable and patient-compliant dosage forms. These forms, for the purposes of the present invention are derived for oral administration. Micronization techniques offer an advantage over larger forms of compounds and poorly soluble compounds—following micronization, compounds have higher surface area to volume ratio. This provides for, as compared to physically coarse compounds, an ultrafine micronized powder that has a significantly increased total surface area. Mathematically, cross-sectional surface area increases with the square of the radius, while volume increases with the cube of the radius. Therefore, as a particle becomes smaller, the volume of the particle decreases at a faster rate than the surface area leading to an increase in the ratio of surface area to volume. By way of theoretical calculations, decreasing the size of a particle can increase its rate of dissolution via increasing the surface area to volume ratio. In the case of solubility, this increase in relative surface area allows for greater interaction with solvent. Further to such additional embodiments, the components of the present invention may be present in portions fine-milled to varying degrees thereby providing a multi-phasic dissolution profile as is disclosed in the preceding application reference.

Although the preceding specification describes how the energy status of a mammal is improved by enhancing the usage of lactate as a fuel source comprising the aforementioned lactate shuttle through increasing adrenergic receptor agonist epinephrine levels via administration of caffeine or similarly acting adrenergic receptor agonist, it should not be construed as the only mechanism by which adrenergic receptor agonists may be modulated to enhance lactate usage. From consideration of the specification, those of skill in the art may determine other methods wherein adrenergic receptor agonists may be employed to enhance lactate usage and the lactate shuttle system.

Although the following examples illustrate the practice of the present invention in three of its embodiments, the examples should not be construed as limiting the scope of the invention. Other embodiments will be readily apparent to one of skill in the art from consideration of the specifications and examples.

EXAMPLES

Example 1

A nutritional supplement is provided in the form of a capsule for use by individuals engaged in regular physical activity wishing to improve athletic performance. Each serving of the nutritional supplement comprises the following:
  about 220 mg of anhydrous caffeine and about 100 mg of pyruvate. One serving is taken by the individual about 30 minutes prior to physical activity in order to enhance the usage of lactate for energy during the ensuing period of physical activity.

Example 2

A nutritional supplement is provided in the form of a liquid capsule for use by individuals engaged in regular endurance training wishing to increase endurance and exercise duration. Each serving of the nutritional supplement comprises the following:
  about 100 mg of caffeine, about 1000 mg L-glutamine and about 10 mg of ethyl pyruvate.
One serving is taken three to five times daily to enhance the availability of lactate for energy.

Example 3

A nutritional supplement is provided in the form of a sustained-release capsule for use by individuals engaged intense endurance training wishing to improve athletic performance. Each serving of the nutritional supplement comprises the following:
  about 250 mg of caffeine, about 5.0 g of L-leucine, about 500 mg L-glutamine, about 10 mg of ethyl pyruvate, about 10 mg of methyl pyruvate and about 10 mg of methyl succinate.
One serving is taken twice daily, once upon waking and once again midday, to enhance the availability and usage of lactate for energy throughout the day.

Extensions and Alternatives

In the foregoing specification, the invention has been described with specific embodiments thereof; however, it will be evident that various modifications and changes may be made thereto without departing from the broader spirit and scope of the invention.

What is claimed:

1. A composition for increasing exercise-induced lactate production for energy in a mammal comprising one or more lactate precursors; and one or more insulinotropic agents.

2. The composition of claim 1 further comprising one or more adrenergic agonists.

3. The composition of claim 2 wherein the one or more adrenergic agonists is selected from the group consisting of dopamine, epinephrine and norepinephrine.

4. The composition of claim 3 wherein the dopamine is present in amount from about 0.01 mg to 2 mg, the epinephrine is present in amount from about 0.01 mg to 2 mg or the norepinephrine is present in amount from about 0.01 mg to 2 mg.

5. The composition of claim 3 wherein the lactate precursor is selected from the group consisting of glutamine and pyruvate; and wherein the insulinotropic agent is selected from the group consisting of: leucine, arginine, methyl pyruvate, methyl succinate, and carbohydrate.

6. The composition of claim 5 wherein the lactate precursor is glutamine; and the insulinotropic agent is leucine.

7. The composition of claim 6 wherein the amount of glutamine is from about 0.05 g to about 5.00 g and the amount of leucine is from about 10 mg to about 7.50 g.

8. The composition of claim 5 wherein the lactate precursor is glutamine; and the insulinotropic agent is arginine.

9. The composition of claim 8 wherein the amount of glutamine is from about 0.05 g to about 5.0 g and the amount of arginine is from about 50 mg to about 5.0 g.

10. The composition of claim 5 wherein the lactate precursor is pyruvate; and the insulinotropic agent is leucine.

11. The composition of claim 10 wherein the amount of pyruvate is from about 1 mg to about 1000 mg and the amount of leucine is from about 10 mg to about 7.5 g.

12. The composition of claim 5 wherein the lactate precursor is pyruvate; and the insulinotropic agent is arginine.

13. The composition of claim 12 wherein the amount of pyruvate is from about 1 mg to about 1000 mg and the amount of arginine is from about 50 mg to about 5.0 g.

14. The composition of claim 2 wherein the one or more adrenergic agonists are beta-adrenergic agonists or alpha-adrenergic agonists.

15. The composition of claim 5 wherein the carbohydrate is glucose.

16. A method of increasing exercised-induced lactate production for energy in a mammal comprising the step of administering to the mammal with exercise a composition comprising one or more lactate precursors and one or more insulinotropic agents.

17. The method of claim 16 further comprising one or more adrenergic agonists.

18. The method of claim 17 wherein the one or more adrenergic agonists is selected from the group consisting of dopamine, epinephrine and norepinephrine.

19. The method of claim 18 wherein dopamine is present in amount from about 0.01 mg to 2 mg, epinephrine is present in amount from about 0.01 mg to 2 mg or norepinephrine is present in amount from about 0.01 mg to 2 mg.

20. The method of claim 16 wherein the lactate precursor is selected from the group consisting of glutamine and pyruvate; and the insulinotropic agent is selected from the group consisting of leucine, arginine, methyl pyruvate, methyl succinate, and carbohydrate.

21. The method of claim 20 wherein the lactate precursor is glutamine; and the insulinotropic agent is leucine.

22. The method of claim 21 wherein the amount of glutamine is from about 0.05 g to about 5.00 g; and the amount of leucine is from about 10 mg to about 7.50 g.

23. The method of claim 20 wherein the lactate precursor is glutamine; and the insulinotropic agent is arginine.

24. The method of claim 23 wherein the amount of glutamine is from about 0.05 g to about 5.0 g and the amount of arginine is from about 50 mg to about 5.0 g.

25. The method of claim 20 wherein the lactate precursor is pyruvate and the insulinotropic agent is leucine.

26. The method of claim 25 wherein the amount of pyruvate is from about 1 mg to about 1000 mg and the amount of leucine is from about 10 mg to about 7.5 g.

27. The method of claim 20 wherein the lactate precursor is pyruvate and the insulinotropic agent is arginine.

28. The method of claim 27 wherein the amount of pyruvate is from about 1 mg to about 1000 mg and the amount of arginine is from about 50 mg to about 5.0 g.

29. The method of claim 17 wherein the one or more adrenergic agonists are selected from the group consisting of beta-adrenergic agonists or alpha-adrenergic agonists.

30. The method of claim 20 wherein the carbohydrate is glucose.

* * * * *

UNITED STATES PATENT AND TRADEMARK OFFICE
CERTIFICATE OF CORRECTION

PATENT NO. : 8,101,569 B2
APPLICATION NO. : 12/829438
DATED : January 24, 2012
INVENTOR(S) : Jason Peters et al.

It is certified that error appears in the above-identified patent and that said Letters Patent is hereby corrected as shown below:

In the Claims:

Column 11, Claim 5, line 1:

"The composition of claim 3" should read --The composition of claim 1--

Signed and Sealed this
Eighteenth Day of June, 2013

Teresa Stanek Rea
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 8,101,569 B2 | Page 1 of 1 |
| APPLICATION NO. | : 12/829438 | |
| DATED | : January 24, 2012 | |
| INVENTOR(S) | : Jason Peters et al. | |

It is certified that error appears in the above-identified patent and that said Letters Patent is hereby corrected as shown below:

In the Claims:

Column 11, line 11 (Claim 5, line 1)

"The composition of claim 3" should read --The composition of claim 1--

This certificate supersedes the Certificate of Correction issued June 18, 2013.

Signed and Sealed this
Sixteenth Day of July, 2013

Teresa Stanek Rea
*Acting Director of the United States Patent and Trademark Office*